United States Patent [19]  
Malhotra et al.

[11] Patent Number: 4,599,105  
[45] Date of Patent: Jul. 8, 1986

[54] 2-[16-(3-FLUORO-5-TRIFLUOROMETHYL-PYRIDINYL-2-OXY)-3-NITRO-PHENOXY]-PROPIONIC ACID DERIVATIVES, HERBICIDAL COMPOSITIONS CONTAINING SAME AND HERBICIDAL METHOD OF USE

[75] Inventors: Sudarshan K. Malhotra, Walnut Creek; B. Clifford Gerwick, III, Concord, both of Calif.

[73] Assignee: The Dow Chemical Company, Midland, Mich.

[21] Appl. No.: 506,135

[22] Filed: Jun. 20, 1983

[51] Int. Cl.$^4$ .................... C07D 213/64; A01N 43/40
[52] U.S. Cl. ........................................ 71/94; 546/291; 546/294; 546/300; 546/302

[58] Field of Search ...................... 546/293, 300, 302; 71/94

[56]         References Cited
      U.S. PATENT DOCUMENTS 4,235,621 11/1980 Nishiyama et al. ...................... 71/94
4,308,053 12/1981 Cartwright et al. .................... 71/94
4,329,167  5/1982 Rempfler et al. ....................... 71/94
4,565,568  1/1986 Johnston et al. ....................... 71/94

Primary Examiner—Alan L. Rotman

[57] ABSTRACT

Novel compounds, e.g., N-methanesulfonyl 2-((5-(3-fluoro-5-(trifluoromethyl)-2-pyridinyl)oxy)-2-nitro-5-phenoxy)propionamide are selective herbicides useful for controlling weeds in valuable crops.

6 Claims, No Drawings

2-[16-(3-FLUORO-5-TRIFLUOROMETHYL-PYRIDINYL-2-OXY)-3-NITRO-PHENOXY]-PROPIONIC ACID DERIVATIVES, HERBICIDAL COMPOSITIONS CONTAINING SAME AND HERBICIDAL METHOD OF USE

BACKGROUND OF THE INVENTION

An active area of agricultural research is devoted to the production of more productive plant life, especially that plant life associated with food sources for man. One aspect of that research is the search for more efficient and more selective herbicides to control undesired vegetation in the presence of valuable crops, thereby reducing the competition for water, sunlight and nutrients and increasing yields.

DESCRIPTION OF THE PRIOR ART

U.S. Pat. No. 4,329,167 describes and claims certain pyridyloxy-phenoxy-alkane carboxylic acid derivatives, U.S. Pat. No. 4,308,053 describes and claims certain 2-pyridinyloxy-N-lower-alkane-sulfonyl benzamides and their use as herbicides, U.S. Pat. No. 4,093,446 describes and claims herbicidal 4-trifluoromethyl-4-nitrodiphenylethers, U.S. Pat. No. 4,233,054 describes new phenoxy-alkanecarboxylic acid derivatives having herbicidal action and U.S. Pat. No. 4,348,221 describes and claims certain herbicidal derivatives of pyrid-2-yloxyphenoxy acetic acids and esters and their use for selective control of weeds in cereals or rice. Copending application Ser. No. 380,840, filed June 18, 1982, describes and claims certain fluoro-substituted pyridyl(oxy/thio)phenoxy compounds having herbicidal activity. Other related compounds are disclosed and claimed in copending application Ser. No. 434,994 filed on Oct. 18, 1982.

SUMMARY OF THE INVENTION

The present invention is directed to novel compounds having herbicidal activity and which correspond to the formula

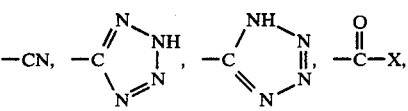

wherein
- X is $CF_3$, $CHF_2$, $CClF_2$, Br, Cl or F;
- Y is Br, Cl or F, provided that at least one of X and Y is F;
- Z is halogen, cyano or nitro;
- A and A' are independently O, S, S=O, $SO_2$, NH or N-alkyl;
- R is H or lower alkyl;
- $R^1$ is a moiety that can be hydrolyzed and/or oxidized in plants or soil to a carboxyl moiety that is present in undissociated or dissociated form; and
- R and $R^1$ together may form a 5- or 6-membered heterocyclic ring, preferably containing oxygen. Preferably $R^1$ is a monovalent organic radical which may contain N, O or S atoms. The optically active isomers are also included in this invention.

A variety of herbicidal compounds containing substituted pyridyl and phenoxy moieties joined via a bivalent —O— or —S— are described in the art. For example, U.S. Pat. Nos. 4,046,553; 4,317,913; 4,267,336; 4,213,774; 4,324,627, 4,309,547 and 4,325,729 and U.S. patent application Ser. Nos. 262,063 and 261,109, both filed July 30, 1980; Ser. No. 817,943, filed July 22, 1977 and Ser. No. 918,550, filed June 23, 1978, all describe such compounds and are incorporated herein by reference. In general, the moieties bonded to the pendant —O— group of the phenoxy in the herbicidal compounds described in these references will also be suitable as the monovalent organic radical represented by

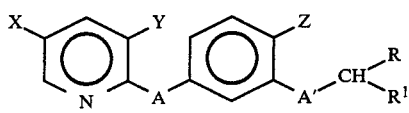

in the formula for the aforementioned novel compounds.

Advantageously, R is H or a $C_1$–$C_3$ alkyl group.

$R^1$ moieties include, but are not limited to $$-(Y')_n R^2$$

wherein Y' is a saturated or unsaturated alkyl group containing an even number of carbon atoms, preferably from 2 to 18 carbon atoms, n is 0 or 1, and $R^2$ is selected from moieties corresponding to one of the following formulae:

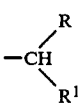

wherein X is halogen, or CN,

wherein M is a metallic cation, ammonium or an organic amine cation typically, but not exclusively, containing alkyl (saturated or unsaturated), alicyclic, heterocyclic or aromatic groups, all unsubstituted or substituted with various other groups not limited to, but including, halo, cyano, nitro and unsubstituted or substituted thiol, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl,

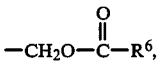

-continued

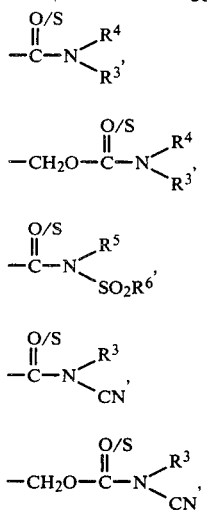

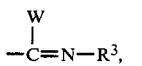

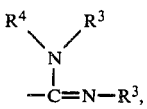

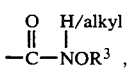

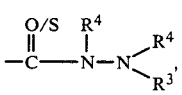

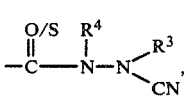

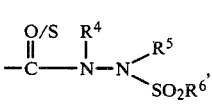

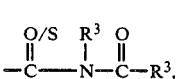

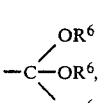

—C(SR$^6$)$_3$

—C(OR$^6$)$_2$,

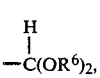

—C(SR$^6$)$_2$,

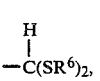

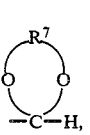

-continued

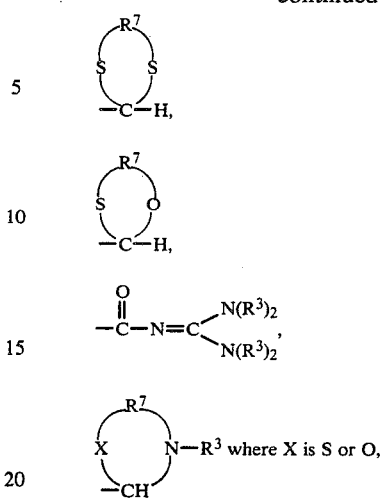

where W is halogen; R$^3$ is H or R$^6$; R$^4$ is H, alkoxy or R$^6$; R$^5$ is H, a metallic cation or R$^6$; and R$^6$ is an alkyl (saturated or unsaturated), alicyclic, heterocyclic or aromatic group, unsubstituted or substituted with various other groups not limited to, but including, halo, cyano, nitro and unsubstituted or substituted thiol, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl,

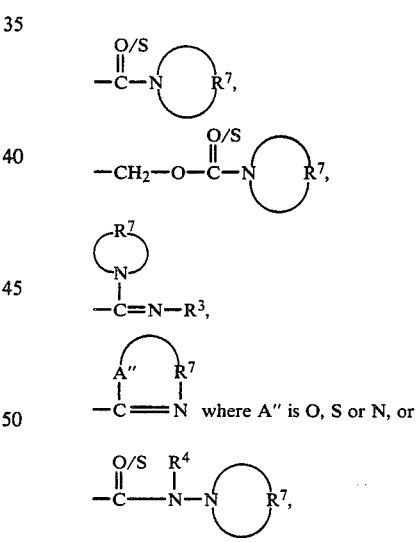

where R$^7$ completes an unsubstituted or substituted saturated heterocyclic ring system.

In the above formulae, the alkyl, alkoxy, alkenyl and alkynyl groups preferably contain 1 to 6 carbon atoms, the alicyclic groups preferably contain 3 to 6 carbon atoms and the aromatic moiety is preferably a 6 carbon ring, although other aromatic ring systems, including heterocyclic ring systems, may be employed, if desired.

In the formula for the aforementioned novel compounds, X is preferably CF$_3$, Y is preferably F, A and A' are preferably O and Z is preferably NO$_2$. Preferred are the compounds in which R is CH$_3$ and R$^1$ is

wherein R" is preferably a $C_1$–$C_6$ alkyl group; the most preferred compounds being methane sulfonamide derivatives and their salts.

The above derivatives can be made by processes generally known to those skilled in the art and as described in the above-mentioned patents. For example, the corresponding acid chlorides can be reacted with a Grignard reagent to make the desired aldehyde or ketone derivative. Similarly, reaction of an acid chloride with KSH will provide the desired thiol acid. Thioamides may be prepared from the corresponding amide by reaction with $P_2S_5$ or, if hydrogen is present on the nitrogen atom, the carbonyl may be converted to, e.g., chloride, with removal of HCl, followed by reaction with hydrogen sulfide. Carbamoyl chlorides are available in the art or they may be prepared from the desired amine and phosgene or thiophosgene for use in making compounds containing the

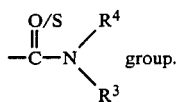

The reaction of an amine with a sulfonyl chloride, e.g., $R^5NH_2 + R^6SO_2Cl$ provides the group

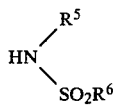

for use in reacting with an appropriate acid chloride.
The reaction of an amine with BrCN provides, e.g.,

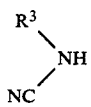

which reacts with the appropriate acid chloride to provide compounds containing the

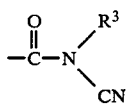

moiety. $P_2S_5$ is employed to make the corresponding S-containing compound.

Reaction of the above cyanoamine with phosgene or thiophosgene provides

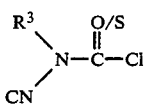

for use in making the corresponding derivatives.
The reaction of the compounds having the moiety

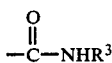

with $PCl_5$ will provide compounds having the moiety

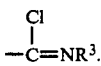

The reaction of the corresponding acid chloride with $RONH_2$ will provide compounds having the group

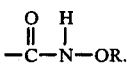

The compounds of formula (I) are useful both as pre- and postemergence broadleaf herbicides, especially in the presence of soybeans. Certain of these compounds are also useful in the presence of corn. Preemergence herbicides are used to treat the soil in which a crop is to be planted, by application before or during seeding, or after seeding and before the crop emerges. Postemergence herbicides are applied after the crop plants and weeds have emerged from the soil. Compounds of formula (I) may be used as selective herbicides in a variety of crops including, for example, soybeans, peanuts, peas, wheat, barley, corn and rice and have shown particularly advantageous benefits in foliar applications to control problem broadleaf weeds in soybeans and, in some cases, corn as well. They may also be used as total herbicides. They may be applied by any of the conventional techniques for applying herbicides. When applied as preemergence herbicides they may, for example, be sprayed on the surface of the soil before or during seeding, or after seeding and before emergence of the crop. In some situations, for example, in preemergence application to soybean crops it may be advantageous to incorporate the compound of the invention into the soil before planting the crop. This may be done by applying the compound to the surface of the soil and then discing or harrowing the soil to mix the compound with the soil.

The compounds of formula (I) may be combined with other selective herbicides to achieve broadspectrum weed control in crops, for example, crops of soybean. Alternatively, the second herbicide component may be a nonselective herbicide chosen to enhance the power of the compound of formula I as a total vegetation control herbicide.

Examples of herbicides for use in admixture with compounds of formula (I) include, but are not restricted to, the following:

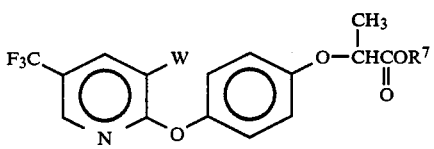

where W is H, Cl or F, and $R^7$ is hydrogen or a salt, ester, thioester or amide derivative of the carboxylic acid.

The compounds employed in the method of the present invention are novel compounds and may be prepared using the requisite starting materials by the following illustrative methods.

EXAMPLE 1

Preparation of 3-((3-fluoro-5-(trifluoromethyl)-2-pyridinyl)oxy)phenol

The disodium salt of resorcinol was prepared from 5.24 g resorcinol and 4 g of 50 percent NaH dispersed in paraffin which was washed with hexane to remove any paraffin. The salt was suspended in 150 ml of DMSO by stirring at ambient temperature for one-half hour after which 4 g of 2,3-difluoro-5-trifluoromethylpyridine were added. Stirring was continued at ambient temperature for three hours. The reaction mixture was diluted with water, acidified with dilute HCl and extracted with ether. The ether extract was washed with water, dried over anhydrous $MgSO_4$ and concentrated to a brown oil which was shown by NMR and GC to consist mainly of the desired product, the main impurity being the starting material. The brown oil was dissolved in $CH_2Cl_2$ and filtered through a 6 inch layer of silica gel. The eluent, a colorless solution, was concentrated to an oil which solidified on standing to give a white crystalline material (4.5 g) having a melting point of 112°–114° C.

EXAMPLE 2

Preparation of ethyl 2-((5-(3-fluoro-5-(trifluoromethyl)-2-pyridinyl)oxy)-2-nitrophenoxy)propionate An ice cooled solution of 2 g of the product from Example 1 in 50 ml of $CH_2Cl_2$ was prepared and 2 ml of 90 percent $HNO_3$ were added. After stirring for about one-half hour at about 5° C., the reaction mixture was diluted with water and extracted with $CH_2Cl_2$. The extract was filtered through a layer of silica gel and the filtrate was concentrated to a thick yellow oil which was shown by GC and NMR to consist mostly of the 2-nitrophenol isomer, i.e., 5-(3-fluoro-5-(trifluoromethyl)-2-pyridinyl)oxy-2-nitrophenol. A mixture of 1.7 g of this nitrophenol and 290 mg of NaH (50 percent dispersed in paraffin, which was washed with hexane to remove paraffin) in 100 ml of DMSO (dimethylsulfoxide) was stirred at ambient temperature for 15 minutes after which 1.2 g of ethyl α-bromopropionate was added. The mixture was heated at 100° C. for one hour while stirring, then cooled, diluted with water and extracted with trichloroethane. The extract was washed with water, dried over anhydrous $MgSO_4$ and concentrated to an oil which was subjected to Kugelrohr distillation to remove any impurities with boiling points up to 145°–150° C. at 18 mm of Hg. A light brown oil (1.5 g) was obtained which was further purified by liquid chromatography and characterized as the desired product by NMR.

| Analysis: | C | H | N |
|---|---|---|---|
| Calculated | 48.8 | 3.35 | 6.67 |
| Found | 49.45 | 3.42 | 6.47 |

EXAMPLE 3

Preparation of 2-(5-fluoro-2-nitrophenoxy)propionic acid using lactic acid

44 Grams (0.28 mole) of 2,4-dinitrobenzene and 25 g (0.28 mole) of lactic acid were dissolved in 200 ml of DMSO and added slowly to a slurry of 14 g (0.58 mole) of sodium hydride in 200 ml of DMSO. Ice bath cooling was required to control the temperature. After stirring until all foaming had subsided, the mixture was cooled, acidified with concentrated HCl and worked up in ether. The residue from stripping the ether extract was crystallized from chloroform to give 19.8 g (31 percent) of the desired product. M.P.=143°–145° C. IR and NMR spectra supported the identification.

| Analysis: | % C | % H | % N |
|---|---|---|---|
| Calculated | 47.17 | 3.52 | 6.11 |
| Found | 46.41 | 3.36 | 5.89 |

EXAMPLE 4

Preparation of 2-(5-hydroxy-2-nitrophenoxy)propionic acid

5 Grams (21.8 moles) of 2-(5-fluoro-2-nitrophenoxy)propionic acid was heated for two hours with 5 ml of 25 percent (by weight) aqueous sodium hydroxide and 100 ml of DMSO and allowed to stand overnight. The mixture was diluted with water and extracted with 1,1,1-trichloroethane (organic discarded), then with ether. The aqueous layer was acidified and extracted with ether. The ether solution was stripped to give 2.5 g of solid product which was recrystallized from ethanol/chloroform to give 1.7 g (35 percent) of the desired product. M.P.=190°–195° C. NMR and IR spectra supported the identification.

| Analysis: | % C | % H | % N |
|---|---|---|---|
| Calculated | 47.58 | 3.99 | 6.19 |
| Found | 47.29 | 3.84 | 6.04 |

EXAMPLE 5

Preparation of 2-((5-(3-fluoro-5-(trifluoromethyl)-2-pyridinyl)oxy)-2-nitro-5-phenoxy)propionic acid 5.4 Grams (23.8 moles) of 2-(5-hydroxy-2-nitrophenoxy)propionic acid was added slowly in DMSO solution to a stirring slurry of 1.25 g (52.1 mmoles) of sodium hydride. 4.4 Grams (24.0 mmoles) of 2,3-difluoro-5-(trifluoromethyl)pyridine was then added with continued stirring. The mixture was heated at 85° C. until it became cloudy and then cleared (30–45 minutes), after which it was cooled and worked up in ether after acidification with HCl. Addition of chloroform to the ether solution caused the starting material to precipitate. The ether solution was stripped to yield a solid which recrystallized from toluene to give 5.4 g (58 percent) of the desired product. M.P.=105.5°–108.0° C. IR and NMR spectra supported the identification. Yield was later improved to 82 percent.

| Analysis: | % C | % H | % N |
|---|---|---|---|
| Calculated | 46.16 | 2.58 | 7.18 |
| Found | 46.38 | 2.44 | 7.18 |

EXAMPLE 6

Preparation of 2-(5-fluoro-2-nitrophenoxy)propionic acid using lithium lactate 9.6 Grams (0.1 mole) of lithium lactate was added portionwise to a slurry of 5.2 g (0.108 mole) of sodium hydride in 50 ml of DMSO with stirring. After an additional hour of stirring, 15.9 g (0.1 mole) of 2,4-difluoronitrobenzene was added and the mixture stirred overnight.

The mixture was diluted with water and the product extracted in an ether workup. It was recrystallized from chloroform to give 9.5 g (42 percent) of the desired product. M.P.=134.5°–143° C. NMR and IR spectra confirmed the structure of the product and was found to be identical with the product obtained in Example 3.

The product from Example 6 was hydrolyzed to 2-(5-(hydroxy-2-nitrophenoxy)propionic acid employing 25% aqueous sodium hydroxide in dioxane and working up generally as described in Example 4. The product had a melting point of 194°–196° C.

EXAMPLE 7

Preparation of 2-((5-(3-fluoro-5-(trifluoromethyl)-2-pyridinyl)oxy)-2-nitro-5-phenoxy)propionamide: N-methanesulfonyl-1

10 Grams (25.6 mmoles) of 2-((5-(3-fluoro-5-(trifluoromethyl)-2-pyridinyl)oxy)-2-nitro-5-phenoxy)propionic acid was heated at 80° C. for two hours with 8 ml (0.11 mole) of thionyl chloride and a few drops of DMF in 125 ml of benzene. The solvent was stripped and 2.4 g (25.2 mmoles) of methanesulfonamide and 100 ml of pyridine added. The resulting mixture was stirred overnight. Pyridine was then stripped and the residue worked up in aqueous HCl solution and ether. A solid separated out. It was filtered off, washed with water and ether, dried and was characterized as the desired product. The ether solution was treated with 10 percent NaOH solution. The aqueous layer was washed with more ether before being acidified, whereupon more product separated. It was filtered and dried. The two solids melted at 165°–167° C. Yield: 6.6 g=55 percent. IR and NMR spectra supported the identification.

| Analysis: | % C | % H | % N |
|---|---|---|---|
| Calculated | 41.11 | 2.80 | 8.99 |
| Found | 40.46 | 2.65 | 8.87 |

EXAMPLE 8

Preparation of 2-(2-nitro-5-(3-fluoro-5-trifluoromethyl-2-pyridyloxy)-phenoxy)-propionic acid: hexyl ester 2-(2-Nitro-5-(3-fluoro-5-trifluoromethyl-2-pyridyloxy)phenoxy)propionic acid (20 g, 0.05 mole) was stirred with thionyl chloride (15 ml, 0.2 mole) in benzene (200 ml) containing a few drops of DMF then heated at reflux for 30 minutes. The benzene and excess thionyl chloride were stripped in vacuo and the residue dissolved in n-hexanol (200 ml). After standing overnight at room temperature, the alcohol was stripped in vacuo and the residue dissolved in ether, water washed, dried and stripped in vacuo. The product solidified on cooling. M.P. 46°–49° C. Yield: 22.9 g (94%). The structure was confirmed by NMR and IR spectroscopy.

| Analysis: | | |
|---|---|---|
| Calculated for $C_{21}H_{22}F_4N_2O_6$: | C = 53.16, H = 4.67, N = 5.91. |
| Found: | C = 53.49, H = 4.65, N = 5.52. |

Employing the above described procedures the following compounds were prepared.

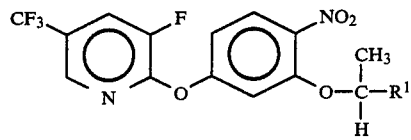

| Number | $R^1$ | m.p., °C. | Refractive Index | Calculated C | H | N | Found C | H | N |
|---|---|---|---|---|---|---|---|---|---|
| 1 | CH₃<br>\|<br>CO₂—C—CO₂C₂H₅<br>\|<br>H | | 1.5108 | 48.98 | 3.70 | 5.71 | 48.32 | 3.45 | 5.96 |
| 2 | CO₂CH₂CH₂OCH₃ | | 1.5165 | 48.22 | 3.60 | 6.75 | 47.70 | 3.51 | 6.17 |
| 3 | CO₂CH₂CH₂OC₂H₅ | | 1.5097 | 49.35 | 3.92 | 6.06 | 49.10 | 3.86 | 5.98 |
| 4 | CO₂CH₃ | 76.5–77.5 | | 47.53 | 2.99 | 6.93 | 47.05 | 2.80 | 6.91 |
| 5 | CO₂(CH₂)₃CH₃ | 65–66 | | 51.12 | 4.06 | 6.28 | 51.33 | 3.98 | 6.20 |
| 6 | CO₂(CH₂)₅CH₃ | 44.5–46 | | 53.16 | 4.67 | 5.91 | 53.49 | 4.65 | 5.52 |
| 7 | CO₂(CH₂)₇CH₃ | | 1.4985 | 54.98 | 5.22 | 5.58 | 55.80 | 5.40 | 5.22 |
| 8 | CO₂CHC₂H₅<br>\|<br>C₂H₅ | | 1.5068 | 54.43 | 4.52 | 5.71 | 51.62 | 4.47 | 5.32 |
| 9 | CO₂CH(CH₂)₄CH₃<br>\|<br>CH₃ | | 1.5005 | 54.10 | 4.95 | 5.74 | 53.97 | 4.93 | 5.64 |
| 10 | CO₂CH₂CH(CH₂)₃CH₃<br>\|<br>C₂H₅ | | 1.5025 | 54.98 | 5.22 | 5.58 | 55.10 | 5.28 | 5.42 |

-continued

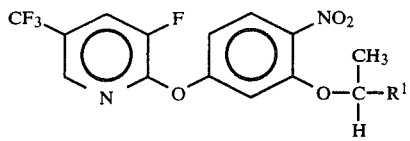

| Number | R¹ | m.p., °C. | Refractive Index | Calculated C | H | N | Found C | H | N |
|---|---|---|---|---|---|---|---|---|---|
| 11 | CONH₂ | 104–106 | | 46.28 | 2.85 | 10.80 | 45.88 | 2.63 | 10.79 |
| 12 | CONHCH₃ | | 1.5414 | 47.65 | 3.25 | 10.42 | 47.23 | 3.17 | 10.42 |
| 13 | CONHOCH₃ | 132–133 | | 45.83 | 3.13 | 10.02 | 45.69 | 3.07 | 9.91 |
| 14 | CONHSO₂CH₃ | 166–168 | | 41.11 | 2.80 | 8.99 | 40.96 | 2.65 | 8.87 |
| 15 | CONHSO₂—⟨C₆H₄⟩—CH₃ | | | 48.62 | 3.15 | 5.90 | | | |
| 16 | CONH—⟨C₆H₄⟩—CH₃ | | | 55.12 | 3.57 | 8.77 | | | |
| 17 | CONH—⟨C₆H₄⟩—Cl | 175–178 | | 50.46 | 2.82 | 8.41 | 50.28 | 2.91 | 8.51 |
| 18 | CONH—C(CH₃)—CO₂C₂H₅ | | | 49.08 | 3.91 | 8.59 | | | |
| 19 | CO₂(CH₂)₂O(CH₂)₂CH₃ | | 1.5015 | 52.17 | 4.38 | 6.09 | 51.96 | 4.16 | 5.92 |

Employing the above procedures and methods analogous to those in the described prior art and utilizing the appropriate starting materials, the following compounds may be prepared:

| | X | Y | Z | A | A' | R | R¹ |
|---|---|---|---|---|---|---|---|
| 1 | Cl | F | Cl | O | O | CH₃ | CO₂Et |
| 2 | F | F | NO₂ | O | O | CH₃ | CO₂Et |
| 3 | Cl | F | Cl | O | O | CH₃ | CO₂H |
| 4 | CF₃ | F | Cl | O | O | CH₃ | CON(Me)₂ |
| 5 | CF₃ | F | NO₂ | S | O | CH₃ | CO₂Et |
| 6 | CF₃ | F | NO₂ | O | NH | CH₃ | CO₂Et |
| 7 | CF₃ | F | NO₂ | O | NCH₃ | CH₃ | CO₂Et |
| 8 | CF₃ | F | NO₂ | O | O | CH₃ | CO₂—⟨C₆H₅⟩ |
| 9 | Cl | F | NO₂ | O | O | CH₃ | CO₂Et |
| 10 | F | Cl | NO₂ | O | O | CH₃ | CO₂Et |
| 11 | Br | F | NO₂ | O | O | CH₃ | CO₂H |
| 12 | Cl | F | NO₂ | O | O | CH₃ | —C(O)NHS(O)CH₃ |
| 13 | F | F | NO₂ | O | O | CH₃ | —C(=O)—SMe |
| 14 | CF₃ | F | Cl | O | O | H | —CO₂C₂H₅ |
| 15 | F | F | NO₂ | S | O | CH₃ | CN |
| 16 | Cl | F | NO₂ | O | O | CH₃ | —C(=O)—CH₃ |
| 17 | CF₃ | F | CN | O | O | CH₃ | CO₂Et |
| 18 | CHF₂ | F | NO₂ | O | O | CH₃ | CO₂H |
| 19 | CClF₂ | F | NO₂ | O | O | CH₃ | CO₂CH₃ |
| 20 | F | Br | NO₂ | O | O | CH₃ | COONH₄ |
| 21 | CF₃ | F | NO₂ | O | O | CH₃ | CH=CH—CO₂CH₃ |
| 22 | CF₃ | F | NO₂ | O | O | CH₃ | CH₂CH₂—CO₂CH₃ |

The compounds utilized in the method of the present invention provide selective control of broad leaved weeds in valuable crops and give particular and advantageous selective postemergent control of such weeds.

For such uses, unmodified active ingredients of the present invention can be employed. However, the present invention embraces the use of the compounds in composition form with an inert material known in the art as an agricultural adjuvant or carrier in solid or liquid form. Thus, for example, an active ingredient can be dispersed on a finely-divided solid and employed therein as a dust or granule. Also, the active ingredients, as liquid concentrates or solid compositions comprising one or more of the active ingredients can be dispersed in water, typically with aid of a wetting agent, and the resulting aqueous dispersion employed as a spray. In other procedures, the above ingredients can be employed as a constituent of organic liquid compositions, oil-in-water and water-in-oil emulsions or water dispersions, with or without the addition of wetting, dispersing, or emulsifying agents. Suitable adjuvants of the foregoing type are well known to those skilled in the art.

The concentration of the active ingredients in solid or liquid compositions generally is from about 0.0003 to about 95 percent by weight or more. Concentrations from about 0.05 to about 50 percent by weight are often employed. In compositions to be employed as concentrates, the active ingredient can be present in a concentration from about 5 to about 98 weight percent. The active ingredient compositions can also contain other compatible additaments, for example, phytotoxicants, plant growth regulants and other biologically active compounds used in agriculture.

In further embodiments, the compounds of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in the ratio of from 1 to 100 parts of the compound of the present invention with from 100 to 1 parts of the additional compound(s).

The exact rate to be applied is dependent not only on a specific active ingredient being applied, but also on a particular action desired, the plant species to be modified and the stage of growth thereof as well as the part of the plant to be contacted with the toxic active ingredient. Thus, all of the active ingredients of the present invention and compositions containing the same may not be equally effective at similar concentrations or against the same plant species.

In selective postemergent operations a dosage of about 0.01 to about 20 pounds/acre (0.0112–22.4 kg/hectare) is generally applicable, although not all compounds are equally effective and some weeds are more difficult to control.

The following examples illustrate the effects of the compounds of this invention.

EXAMPLE 9

In representative operations, each compound to be utilized in a series of tests is dissolved in acetone to one-half of the final volume (twice the final concentration) to be used and the acetone solution in each case is admixed with an equal volume of water containing 0.1 percent by weight of surface active material. The compositions, generally in the nature of an emulsion, were employed to spray separate respective plant species which had been grown to a 2–4 leaf stage in soil of good nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other plants were left untreated to serve as controls. After treatment, the plants were maintained for about two weeks under greenhouse conditions conducive for good plant growth and watered as necessary. The specific plant species, test compound and dosage and the percent postemergent control obtained are set forth in the table below. Control refers to the reduction in growth compared to the observed results of the same untreated species.

Plant species in these tests were:

| Common Name | Scientific Name |
| --- | --- |
| Soybeans | Glycine max |
| Morning Glory | Ipomoea spp. |
| Velvet Leaf | Abutilon theophrasti |
| Jimson Weed | Datura stramonium |
| Pigweed | Amaranthus spp. |
| Cocklebur | Xanthium spp. |
| Yellow Nutsedge | Cyperus esculentus |
| Barnyardgrass | Echinochloa crusgalli |
| Crabgrass | Digitaria sanquinalis |
| Yellow Foxtail | Setaria lutescens |
| Johnsongrass | Sorghum halepense |
| Wheat | Triticum aestivum |
| Corn | Zea mays |
| Smartweed | Polygonum spp. |
| Lambsquarters | Chenopodium spp. |

POSTEMERGENT CONTROL OF PLANT SPECIES

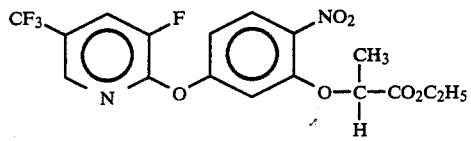

| | Percent Control At Indicated Application Rates (ppm) | | | | |
| --- | --- | --- | --- | --- | --- |
| Species | 125 | 62.5 | 31.25 | 15.6 | 7.8 |
| Soybeans | 25 | 15 | 10 | 5 | 0 |
| Morning Glory | 100 | 75 | 60 | 20 | 0 |
| Velvet Leaf | 100 | 100 | 90 | 40 | 10 |
| Jimson Weed | 100 | 85 | 70 | 30 | 15 |
| Cocklebur | 95 | 90 | 90 | 60 | 10 |
| Yellow Nutsedge | 65 | 45 | 20 | 10 | 0 |

POSTEMERGENT CONTROL OF PLANT SPECIES

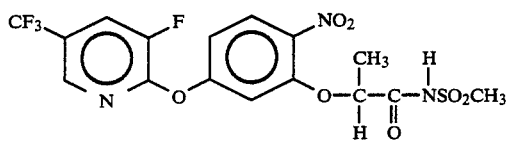

| | Percent Control At Indicated Application Rates (ppm) | | | | | |
| --- | --- | --- | --- | --- | --- | --- |
| Species | 250 | 125 | 62.5 | 31.25 | 15.6 | 7.8 |
| Corn | 10 | 10 | 10 | 0 | NT | NT |
| Soybeans | 25 | 15 | 10 | 10 | 0 | NT |
| Morning Glory | 100 | 100 | 100 | 100 | 75 | 20 |

POSTEMERGENT CONTROL OF PLANT SPECIES

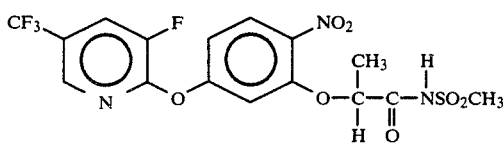

| Species | \multicolumn{6}{c}{Percent Control At Indicated Application Rates (ppm)} | | | | | |
|---|---|---|---|---|---|---|
|  | 250 | 125 | 62.5 | 31.25 | 15.6 | 7.8 |
| Velvet Leaf | 100 | 100 | 100 | 65 | 40 | 0 |
| Jimson Weed | 100 | 100 | 100 | 85 | 50 | 25 |
| Cocklebur | 100 | 100 | 65 | 50 | 40 | 30 |
| Yellow Nutsedge | 99 | 80 | 50 | 30 | 15 | 0 |

POSTEMERGENT CONTROL OF PLANT SPECIES

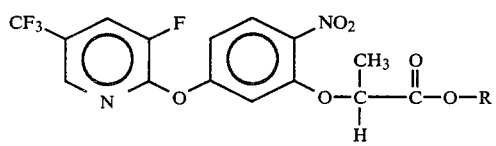

| | Species | \multicolumn{6}{c}{Percent Control At Indicated Application Rates (ppm)} | | | | | |
|---|---|---|---|---|---|---|---|
| | | 500 | 250 | 125 | 62.5 | 31.25 | 15.6 |
| R = H | Soybeans | 10 | 10 | 0 | NT | NT | NT |
| | Cocklebur | 100 | 80 | 100 | 100 | 10 | 0 |
| | Jimson Weed | 100 | 100 | 100 | 100 | 20 | 0 |
| | Lambsquarter | 50 | 40 | 15 | 0 | NT | NT |
| | Pigweed | 100 | 100 | 100 | 40 | 0 | NT |
| | Smartweed | 90 | 100 | 80 | 10 | 0 | NT |
| | Velvet Leaf | 40 | 50 | 0 | NT | NT | NT |
| R = Na | Soybeans | 5 | 10 | 10 | 5 | 0 | NT |
| | Cocklebur | 60 | 100 | 60 | 10 | 0 | NT |
| | Jimson Weed | 100 | 100 | 100 | 100 | 40 | 20 |
| | Lambsquarter | 60 | 50 | 40 | 10 | 0 | NT |
| | Pigweed | 100 | 100 | 100 | 100 | 100 | 0 |
| | Smartweed | 100 | 100 | 100 | 50 | 0 | NT |
| | Velvet Leaf | 60 | 40 | 40 | 15 | 0 | NT |

EXAMPLE 10

So as to clearly illustrate the phytotoxic properties of the various active ingredients of the present invention applied preemergently, a controlled greenhouse experiment is described below.

The seeds of various species of plants were planted in beds of good agricultural soil in a greenhouse. A number of compositions of the present invention, generally in the nature of an aqueous emulsion, were applied at rates listed in the table so as to deposit a predetermined amount of active ingredients uniformly throughout the surface of the bed. Another seed bed was treated only with water to serve as a control. After treatment, the seed beds were maintained for two weeks under greenhouse conditions conducive for good plant growth and watered as necessary. The specific plant species, test compound and dosage and the percent preemergent control are set forth in the table below. Control refers to the reduction in growth compared to the observed results of the same untreated species.

PREEMERGENT CONTROL OF PLANT SPECIES

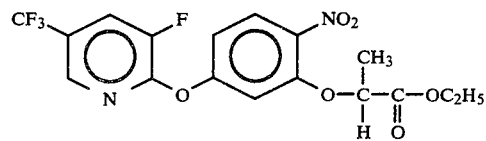

| Species | \multicolumn{5}{c}{Percent Control At Indicated Application Rate (lb/acre)} | | | | |
|---|---|---|---|---|---|
|  | 0.5 | 0.25 | 0.125 | 0.062 | 0.031 |
| Corn | 0 | NT | NT | NT | NT |
| Soybeans | 0 | NT | NT | NT | NT |
| Wheat | 0 | NT | NT | NT | NT |
| Jimson Weed | 100 | 80 | 50 | 10 | 0 |
| Morning Glory | 20 | 0 | NT | NT | NT |
| Pigweed | 50 | 40 | 10 | 0 | NT |
| Velvet Leaf | 20 | 0 | NT | NT | NT |
| Barnyardgrass | 90 | 50 | 10 | 0 | NT |
| Crabgrass | 100 | 100 | 100 | 30 | 0 |
| Johnsongrass | 98 | 80 | 30 | 0 | NT |
| Yellow Foxtail | 100 | 90 | 20 | 0 | NT |
| Yellow Nutsedge | 40 | 0 | NT | NT | NT |

We claim:
1. A compound having the formula

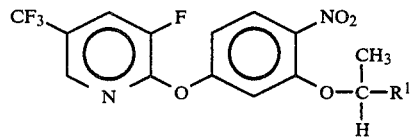

wherein $R^1$ is a carboxylic acid group or an alkali or alkaline earth metal salt thereof.

2. A composition comprising a herbicidally effective amount of a compound having the formula

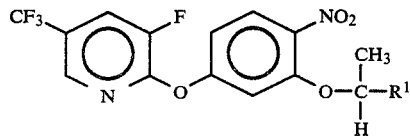

wherein $R^1$ is a carboxylic acid group or an alkali or alkaline earth metal salt thereof in combination with an inert agricultural adjuvant or carrier.

3. The method of controlling undesired plant growth which comprises applying to the locus of said plants a herbicidally effective amount of a compound having the formula

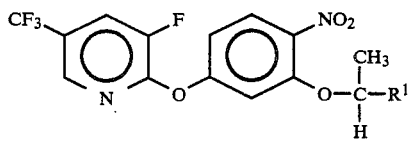

wherein $R^1$ is a carboxylic acid group or an alkali or alkaline earth metal salt thereof.

4. Compound of claim 1 wherein $R^1$ is —COOH.
5. Composition of claim 2 wherein $R^1$ is —COOH.
6. Method of claim 3 wherein $R^1$ is —COOH.

UNITED STATES PATENT AND TRADEMARK OFFICE
CERTIFICATE OF CORRECTION

PATENT NO. : 4,599,105

DATED : July 8, 1986

INVENTOR(S) : Sudarshan K. Malhotra et al.

It is certified that error appears in the above-identified patent and that said Letters Patent is hereby corrected as shown below:

```
Column 6, line 40, "soybeam" should read --soybean--.

Column 10, in the table, subtitle "Number" should read
                -- Compound --.
                   Number Column 13, line 9, "above" should read --active--.
```

Signed and Sealed this

Third Day of March, 1987

Attest:

DONALD J. QUIGG

Attesting Officer

Commissioner of Patents and Trademarks